Figure 1:
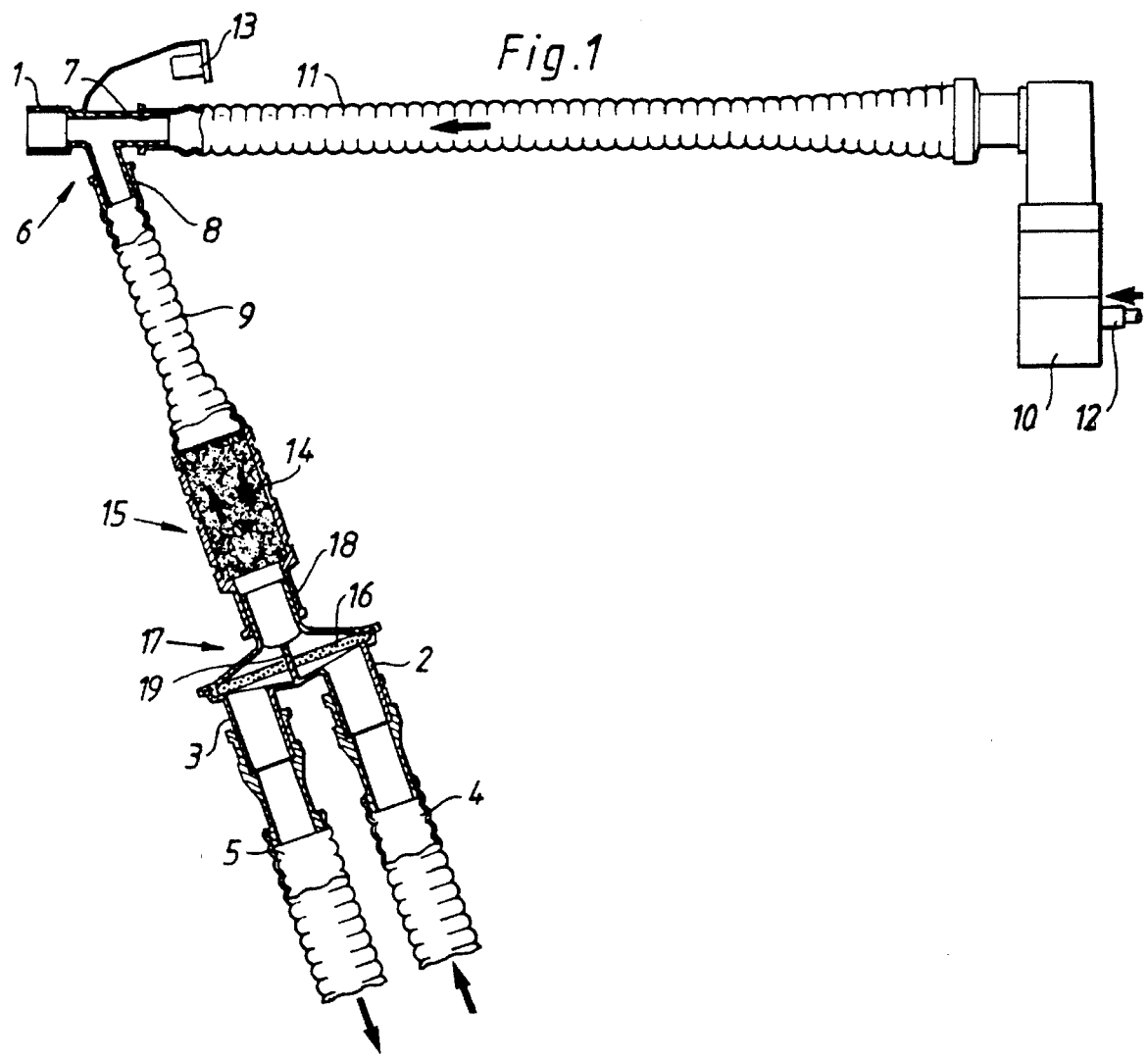

United States Patent [19]

Wikefeldt

[11] Patent Number: 5,546,930
[45] Date of Patent: Aug. 20, 1996

[54] PATIENT CONNECTOR WITH HME, FILTER, AND NEBULIZER CONNECTION

[75] Inventor: Per Wikefeldt, Järfälla, Sweden

[73] Assignee: Engstrom Medical Aktiebolag, Sweden

[21] Appl. No.: 116,014

[22] Filed: Sep. 2, 1993

[30] Foreign Application Priority Data

| Sep. 28, 1992 | [SE] | Sweden | 9202787 |
| Apr. 26, 1993 | [SE] | Sweden | 9301376 |
| Jun. 9, 1993 | [SE] | Sweden | 9301963 |

[51] Int. Cl.⁶ .......................... A62B 18/08; A62B 7/10; A62B 23/02; A61M 16/10
[52] U.S. Cl. ................ 128/201.13; 128/205.12; 128/205.27; 128/204.17; 128/205.29; 128/912; 128/DIG. 26; 128/207.14; 128/203.15; 128/203.12
[58] Field of Search .......... 128/204.18, 200.18, 128/200.21, 203.12, 205.12, 911, 912, 203.15, 203.21, 203.28, 201.13, 205.27, 205.29, 204.17, DIG. 26, 207.14

[56] References Cited

U.S. PATENT DOCUMENTS

| 1,050,484 | 1/1913 | McGerry et al. | 128/201.22 |
| 2,992,645 | 7/1961 | Fowler | 128/203.15 |
| 3,731,691 | 5/1973 | Chen | 128/207.15 |
| 4,240,417 | 12/1980 | Holever | 128/207.15 |
| 4,510,933 | 4/1985 | Wendt et al. | 128/207.14 |
| 4,516,573 | 5/1985 | Gedeon | 128/204.18 |
| 4,747,403 | 5/1988 | Gluck et al. | 128/200.16 |
| 4,829,998 | 5/1989 | Jackson | 128/204.18 |
| 4,838,258 | 6/1989 | Dryden et al. | 128/204.18 |
| 4,852,563 | 8/1989 | Gross | 128/204.18 |
| 4,938,210 | 7/1990 | Shene | 128/204.18 |
| 4,967,744 | 11/1990 | Chua | 128/204.18 |
| 5,069,204 | 12/1991 | Smith et al. | 128/203.15 |
| 5,119,807 | 6/1992 | Roberts | 128/205.12 |
| 5,186,166 | 2/1993 | Riggs et al. | 128/203.15 |

FOREIGN PATENT DOCUMENTS

| 0298389 | 7/1987 | European Pat. Off. | 128/205.12 |
| 0462412 | 12/1991 | European Pat. Off. | 128/DIG. 26 |
| 0533644 | 3/1993 | European Pat. Off. | 128/201.13 |

Primary Examiner—Kimberly L. Asher
Attorney, Agent, or Firm—Lerner, David, Littenberg, Krumholz & Mentlik

[57] ABSTRACT

Patient connection apparatus is disclosed for connecting a patient to a respirator or anesthesia machine. The patient connection apparatus includes a nipple for providing an inhalation-exhalation stream, a Y-piece for dividing the inhalation-exhalation stream into an inhalation conduit and an exhalation conduit, a patient conduit for connecting the nipple to the Y-piece, a heat and moisture exchanger disposed in the patient conduit for exchanging heat and moisture with the inhalation-exhalation stream, and a nebulizer connector located between the nipple and the heat and moisture exchanger for connecting the inhalation-exhalation stream to the nebulizer. In another embodiment, the patient connection apparatus includes an inhalation connector arranged downstream of the heat and moisture exchanger for connecting the patient conduit to the nebulizer. In another embodiment, a powder inhalator is provided in connection with the nipple so that powder can be supplied to the patient.

31 Claims, 3 Drawing Sheets

PATIENT CONNECTOR WITH HME, FILTER, AND NEBULIZER CONNECTION

FIELD OF THE INVENTION

The present invention relates to a patient connector intended for connecting a patient to a respirator and/or to an anesthesia device. More particularly, the present invention relates to a patient connector which includes a patient connection nipple along with two additional nipples which are intended to be connected to an inhalation pipe and an exhalation pipe, respectively. Still more particularly, the present invention relates to such patient connector which includes a heat and moisture exchange device arranged between these nipples.

BACKGROUND OF THE INVENTION

Patient connectors intended for connecting patients to respirators and/or anesthesia devices have in the past suffered from the disadvantage that heat and moisture exchange devices used therein must be removed when the patient is to be given medicine with the help of a nebulizer, i.e., an arrangement which finely divides the medicine into very small droplets. A patient connector of this type is described, for example, in EP-A2-0,462,412, but this device does not describe how this structure can be used together with a nebulizer. It is therefore a primary object of the present invention to provide such a device.

SUMMARY OF THE INVENTION

These and other problems have now been solved by the invention of a patient connection apparatus for connecting a patient to a respirator or anesthesia device which comprises patient connection nipple means for providing an inhalation-exhalation stream, divider means for dividing the inhalation-exhalation stream into an inhalation conduit and an exhalation conduit, patient connection conduit means for connecting the patient connection nipple means to the divider means, heat and moisture exchange means disposed in the patient connection conduit means for exchanging heat and moisture with the inhalation-exhalation stream, and nebulizer connection means located between the patient connection nipple means and the heat and moisture exchange means for connecting the inhalation-exhalation stream with a nebulizer.

In accordance with one embodiment of the patient connection apparatus of the present invention, flexible connector means are provided for flexibly connecting the nebulizer connection means with a nebulizer. Preferably, the flexible connector means comprises a pleated plastic tube.

In accordance with another embodiment of the patient connection apparatus of the present invention, the patient connection nipple means and the nebulizer connection means are combined into a unitary connection means, which unitary connection means includes inhalation-exhalation connection means for connecting the patient connection nipple means with the patient connection conduit means.

In a preferred embodiment of the patient connection apparatus of the present invention, the patient connection conduit means comprises flexible plastic tube means, and the heat and moisture exchange means includes a wad of flexible material which is capable of absorbing heat and moisture from exhaled air and transferring the heat and moisture to the inhaled air. In a preferred embodiment, the wad of flexible material comprises fibrous material.

In accordance with a preferred embodiment of the patient connection apparatus of the present invention, the apparatus includes inhalation connection means arranged in the exhalaration direction downstream of the heat and moisture exchange means for connecting the patient connection conduit means to the nebulizer. In a preferred embodiment, the apparatus includes non-return valve means disposed in the inhalation connection means, whereby exhaled air is prevented from flowing through the inhalation connection means.

In another embodiment of the patient connection apparatus of the present invention, the nebulizer comprises an expansion chamber connected to the inhalation connection means, as well as reservoir means connected to the expansion chamber for supplying a fluid and/or medication for nebulization therein. Preferably, the reservoir means includes pressure means for supplying the fluid and/or medication to the expansion chamber.

In accordance with another embodiment of the patient connection apparatus of the present invention, the apparatus includes powder inhalation means associated with the patient connection nipple means whereby powder can be supplied to the patient thereby. In a preferred embodiment, the apparatus includes inhalation connection means arranged in the exhalation direction downstream of the heat and moisture exchange means for connecting the patient connection conduit means to the nebulizer. Preferably, the powder inhalation means is associated with the inhalation connection means.

In accordance with a preferred embodiment of the patient connection apparatus of the present invention, the inhalation connection means includes non-return valve means for preventing exhaled air from flowing through the inhalation connection means.

In accordance with another embodiment of the patient connection apparatus of the present invention, the powder inhalation means includes gas supply means for supplying gas thereto to aid in supplying the powder. Preferably, the gas supply means is hand actuated, and more preferably comprises a rubber bladder or rubber bellows.

In accordance with this invention, by providing the patient connector with a nebulizer connection arranged between the patient connection nipple and the heat and moisture exchange device, the latter does not need to be removed for administering medication, and moreover, at the same time achieves the advantage that medicine which might be exhaled can be at least partially absorbed, if not totally, or restrained in the heat and moisture exchange device, and thus prevented from reaching the connected respirator and/or anesthesia device. The nebulizer is thus suitably separated from the connection by means of a flexible connection pipe which can, for example, consist of a pleated plastic tube. In this manner, the patient need not be disturbed by the location of the nebulizer, and at the same time, the tube can be used to catch large drops of medicine and/or condensed medicine.

Preferably, the patient connection nipple and the nebulizer connection are arranged on a Y-piece or the like which contains a third connection, which by means of a patient connection portion and a second Y-piece or the like, is connected with the inhalation and exhalation tubes. In this manner, the device can easily be combined with various details to build up a desired patient connector. In accordance with this invention, the device not only provides a complete patient connector but also the significant component details thereof, such as the nipples and the heat and moisture exchange device, which are not necessarily combined upon delivery. It is sufficient, however, if they are arranged so that upon use they form the desired patient connector, i.e., a patient connector according to this invention.

In order to thus bother the patient as little as possible, the patient connection portion can consist of a flexible plastic tube and can contain the heat and moisture exchange device in the form of a wad or the like of flexible material, such as fibrous material, which has the ability to absorb moisture and heat from the exhaled air and transfer this to the inhaled air.

In the case where the second Y-piece comprises a bacteria filter, which is arranged to separate the nipples connected to the inhalation and exhalation pipes from a third nipple connected to the patient connection portion, an additional advantage is obtained in that the exhaled medicine, which has not been caught by the heat and moisture exchange device, is effectively prevented from reaching the respirator and/or anesthesia device.

Another significant advantage is obtained if the nebulizer is arranged separable from the nebulizer connection, which can then be used, for example, for sucking away mucous, something which is often necessary for patients subject to having medication administered in this manner. The nebulizer can thus suitably be provided with a separate closure device, such as a cover. In this manner, the nebulizer does not need to be connected to the patient at all times.

Additional advantages are obtained if the second Y-piece is provided with an intermediate wall which separates the inhalation and exhalation flows therein. In this manner, only half of the bacteria filter will be loaded with possibly exhaled medicine, and the loading can readily be controlled by comparison of the pressure drop in both of the filter halves. In this manner it can be readily determined when the filter should be changed.

In accordance with a preferred embodiment of the present invention in which a connection pipe is arranged downstream of the heat and moisture exchange device, as seen in the direction of exhaled air, the connection pipe is arranged between the main pipe and the nebulizer, such that the inhaled air can be led either wholly or partially through the latter. In this manner, an advantage is obtained in that the nebulization can be achieved, either wholly or partially, with the assistance of the inhaled air. In this embodiment a non-return valve is preferably arranged in the connection pipe to prevent the exhaled air from flowing through the connection pipe. In this manner, total dead volume is reduced, i.e., the exhaled air which is breathed back into the patient.

Further in accordance with this embodiment of the present invention, the nebulizer preferably includes an expansion chamber which is connected both to the connector pipe and to a reservoir for supplying the required medicine or other fluid, such as pure water, for example, for nebulization. In this manner, the necessary components of the nebulizer can have a very simple but highly effective structure. The reservoir is preferably provided with means allowing for pressurization in order to supply the medicine or other fluid such as pure water to the expansion chamber. These means can, for example, be formed by a simple pump arrangement. The connection pipe is also preferably arranged so as to be detachable from the main pipe, whereby means are thus arranged for closing off the connection orifice to the main pipe.

In accordance with another embodiment of the present invention, the apparatus includes a connection orifice for a powder inhaler which is arranged between the patient and the heat and moisture exchange device or parallel with this device. In this manner, another benefit is obtained in that medicine can be supplied even in the form of a powder. This type of connection orifice is preferably arranged in a pipe which is only passed by inhaled air. In this manner, the necessary requirement that the powder inhaler be placed in a dry environment can be met. The air (gas) intake of the powder inhaler is preferably connected to a source of additional air (gas). In this manner, a powder dosing which is independent of the flow and the pressure in the inhaled gas is rendered possible. A simple structure is obtained if this source is formed by a hand pump, such as a rubber bladder or rubber bellows. In that event, this can be connected to a container which is arranged to sealingly enclose the powder inhaler with its powder dosing orifice connected to the connection orifice.

BRIEF DESCRIPTION OF THE DRAWINGS

The following detailed description of the present invention can be more readily understood with reference to the drawings, in which:

FIG. 1 is a side, elevational, partially sectional, perspective view of a patient connection apparatus according to the present invention including a nebulizer coupled thereto;

FIG. 2 is a graphical comparison between the pressure rise in a patient connection apparatus according to the present invention and a corresponding structure in which the heat and moisture exchange device has been removed;

FIG. 3 is a side, elevational, perspective view of another embodiment of the patient connection apparatus of the present invention, including a connection pipe between the main pipe and the nebulizer; and FIG. 4 is a side, elevational, partially sectional perspective view of a powder inhaler for use in connection with the patient connection apparatus of the present invention.

DETAILED DESCRIPTION

Referring to the drawings, in which like numerals refer to like portions thereof, FIG. 1 shows a patient connector, which is intended to connect a patient to a respirator and/or an anesthesia machine (not shown) which comprises a patient connection nipple 1 and two nipples 2 and 3 intended to be connected to an inhalation pipe 4, and an exhalation pipe 5, respectively.

The patient connection nipple 1 is arranged in a first Y-piece 6, which is shown with two additional nipples, namely a nipple 7, which forms the nebulizer connection, and a nipple 8, which is connected to a patient connection portion 9. The nebulizer connection 7 is separated from the actual nebulizer 10 by means of a flexible joining tube 11, which is in the form of a pleated plastic tube. Reference numeral 12 denotes a compressed air line, by means of which the compressed air necessary for nebulization is supplied to the nebulizer 10. The nebulizer 10 is normally filled with requisite medicine or the like. However, it can, of course, alternatively be supplied with compressed air through line 12. The expression "medicine" also includes water, in the situation where it is desired to moisten the patient's lungs and breathing passages.

When the nebulizer is used for supplying water, this should preferably be supplied as an isotonic solution of sodium chloride, or even of other salts in water. This solution moreover should be sterile. In this manner the patient connector according to the present invention can be said to comprise a combination of a passive fluid supply through the heat and moisture exchange device 15, and separate from this an active moisturization device through the nebulizer 10. This represents a significant advantage, particularly as it is used in connection with patients who are treated for a long period of time.

The Y-piece 6 is provided with a cover 13, which fits the connection nipple 7, i.e., the nebulizer connection. In this manner, the nebulizer 10 and the connection pipe 11 can be removed between administrations of medicine which, in and of itself, can be an advantage to the patient. Furthermore, in this manner the nebulizer connection can also be used for other purposes, e.g., for sucking away mucous, something which is often necessary for patients who are subjected to this type of treatment.

The patient connector 9 preferably consists of a pleated flexible plastic tube, which contains the heat and moisture exchange device 15. This device preferably constitutes a wad or the like 14 of a flexible material, e.g., fibers, with the capacity to absorb moisture and heat from the exhaled air and to transfer same to the inhaled air.

Moreover, this device has the function of taking up a major part of any medicine which may be exhaled by the patient and doing so without increasing the resistance to breathing by any appreciable degree. Should any medicine pass the device 15, this is effectively stopped by a bacteria filter 16 arranged in a Y-piece 17, i.e., a Y-piece which comprises the nipples 2 and 3 as well as a third nipple 18 for connection to the patient connection portion 9. This Y-piece is provided with an intermediate wall 19, which separates the inhalation and exhalation flows from each other. In this manner, the necessary dead volume is reduced, i.e., the portion of the exhaled air which is re-supplied to the patient on inhalation. Furthermore, another advantage is obtained in that only one-half of the filter 16 is loaded by medicine which might be exhaled. In this manner, one obtains a difference in the pressure drop on the two filter halves, and this difference can be used to determine when the filter should be replaced.

Figure 2:
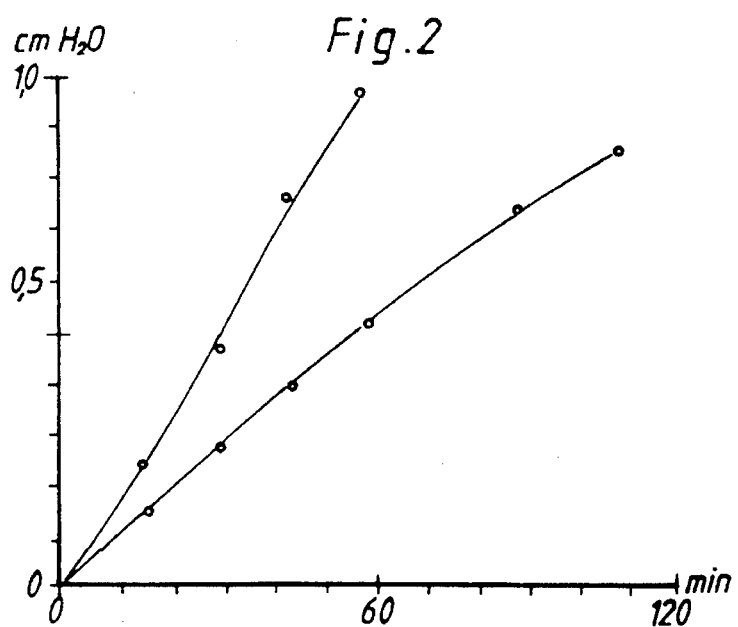

Turning to FIG. 2, there is shown therein the pressure increase in cm $H_2O$ during nebulization for both a complete patient connector according to the present invention, and a corresponding arrangement in which the heat and moisture exchange device has been removed. It should be observed in this regard that the nebulization normally only occurs during the inhalation phase. It is clear from FIG. 2 that a patient connector with the heat and moisture exchange device used in this invention (the lower curve) has a slower rate of pressure rise than a corresponding device without the heat and moisture exchange device (the upper curve). Preferably, the pressure rise should not exceed about 1 cm $H_2O$, but a higher pressure rise is possible, if the total pressure increase in the patient connector is less than about 5 cm $H_2O$, which is still considered to be acceptable.

The illustrated patient connector is not provided with any type of device for sampling the inhaled or exhaled air. However, it will be clear to one of ordinary skill in this field that this device could be provided with a sampling device, such as one of the type described in the aforementioned EP-A2-0,462,412. Furthermore, the form and function of the included components can be varied within wide limits. The invention is thus not limited to the above-described embodiment, but can be varied. For example, the nebulizer connection 7 could alternatively be arranged on the patient connection portion 9 at a point between the wad 14 of the heat and moisture exchange device 15 and the patient. The expression "Y-piece or the like" also includes other components having similar function, e.g., a T-piece or other three-pipe branch distributors.

Figure 3:
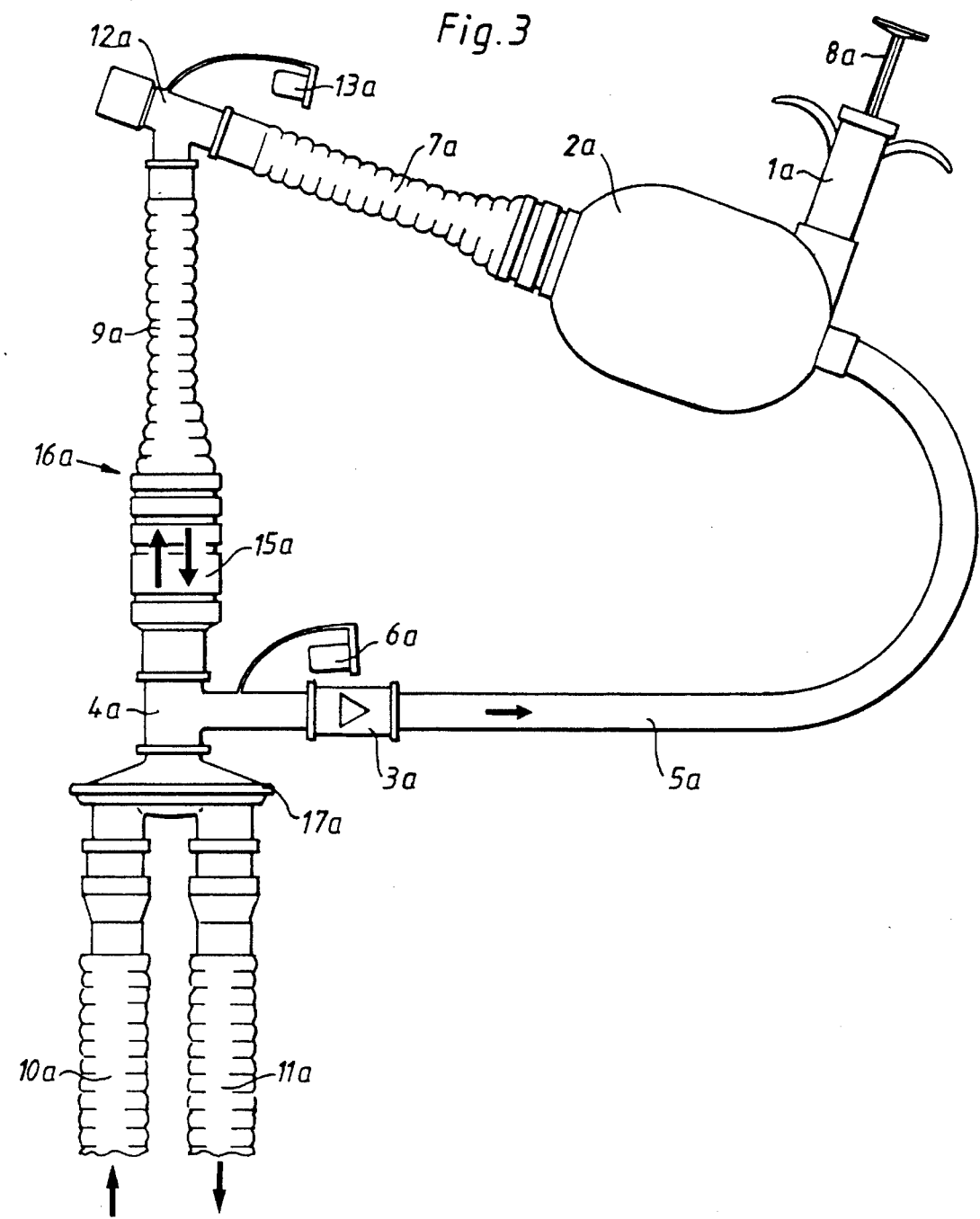

Turning to FIG. 3, in this embodiment of the invention, inhalation air or other suitable gas is supplied through pipe 10a and led away through pipe 11a. These pipes are connected to a Y-piece 17a which can be provided with a filter and intermediate wall in the manner described above. The Y-piece 17 is, in turn, connected to a T-piece 4a which is either connected to a connection tube 5a or closed by a plug 6a. The connection tube 5a is provided with a non-return valve 3a and leads to an expansion chamber 2a, which together with a reservoir 1a forms a nebulizer. The pressure vessel 1a is, in this case, provided with simple means for being pressurized, e.g., a simple pump arrangement 8a. The expansion chamber 2a is, in turn, connected to a nebulizer pipe 7a, which is coupled to a Y-piece 12a. If the nebulizer pipe 7a is disconnected from Y-piece 12a, the latter can then be closed off with the help of a plug 13a. The T-piece 4a is further connected to a heat and moisture exchanger 15a, which is connected with the Y-piece 12a by a flexible hose 9a. The T-piece 4a, the heat and moisture exchanger 15a, and the flexible hose 9a can in this manner be said to form a main pipe 16a.

The patient connector of FIG. 3 is preferably dimensioned such that about half of the inhalation air passes through the expansion chamber 2a. The non-return valve 3a is suitably built directly into the hose 5a. When nebulization is completed, the hose 5a and non-return valve 3a can thus be removed from the T-piece 4a, and the plug 6a can be fitted into place in the T-piece 4a. Because of the presence of non-return valve 3a, the increase in dead volume, as a result of the expansion chamber 2a, the hose 5a and the tube 7a, is minimal.

Figure 4:
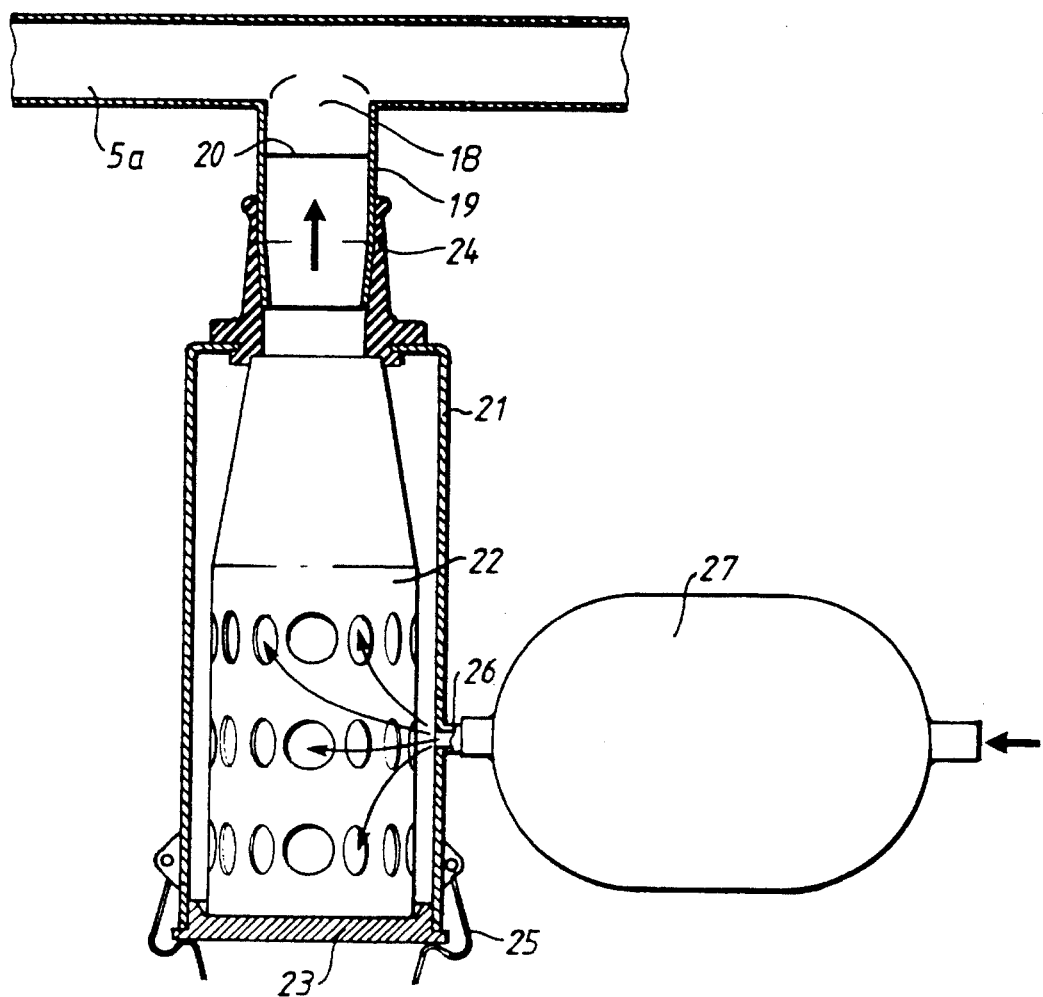

Turning to FIG. 4, reference numeral 5a denotes a connection pipe, e.g., as denoted by the same reference numeral in FIG. 3. Connection pipe 5a in this case has been provided with a connection orifice 18 in a nipple 19. Line 20 denotes a non-return valve, if such should be necessary. In an outer container 21, a powder inhaler 22 is arranged clamped between a bottom plate 23 and a seal 24. The bottom plate 23 is held in place by means of clamps 25. The container 21 is connected, by means of a nipple 26, to a hand pump 27, which for example can be formed by a simple rubber bladder.

The powder inhaler operates in a conventional manner apart from the fact that the air or gas supply can be increased with the help of the hand pump 27, compared to that which is the case with conventional use. This may be required in order to nullify the flow resistance of the patient connector, or in order to increase the dosing.

The powder inhaler used according to the invention is shown in FIG. 4. In practice, however, this can, for example, be formed according to the article "Tubuhaler: A New Powder Inhaler for Administration of Drugs to the Airways," by Kjell Wetterlin, in *Pharmaceutical Research*, Vol. 5, No. 8, 1988.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. An apparatus for connecting a patient to a respiration-anesthesia device, comprising:

patient connection nipple means for directing an inhalation-exhalation stream to a patient;

divider means for separating said inhalation-exhalation stream into an inhalation substream and an exhalation substream;

patient connection conduit means for connecting said patient connection nipple means to said divider means, heat and moisture exchange means for exchanging heat and moisture between said inhalation and exhalation substreams, a respiration-anesthesia device being connected to said heat and moisture exchange means through said inhalation and exhalation substreams, so that said heat and moisture exchange means removes heat and moisture from said exhalation substream and delivers said heat and moisture to said inhalation substream; and nebulizer connection means for connecting said inhalation-exhalation stream to a nebulizer.

2. The patient connection apparatus of claim 1 including flexible connector means for flexibly connecting said nebulizer connection means with said nebulizer.

3. The patient connection apparatus of claim 2 wherein said flexible connector means comprises a pleated plastic tube.

4. The patient connection apparatus of claim 2 wherein said flexible connector means is removably connected to said nebulizer connection means whereby said nebulizer connection means can be utilized for removing mucous from said patient.

5. The patient connection apparatus of claim 4 including nebulizer closure means for closing said nebulizer connection means by removal of said flexible connection means.

6. The patient connection apparatus of claim 1 wherein said patient connection nipple means and said nebulizer connection means are combined into a unitary connection means, and said unitary connection means includes inhalation-exhalation connection means for connecting said patient connection nipple means with said patient connection conduit means.

7. The patient connection apparatus of claim 6 wherein said unitary connection piece comprises a Y-piece.

8. The patient connection apparatus of claim 1 wherein said divider means comprises a Y-piece.

9. The patient connection apparatus of claim 1 wherein said patient connection conduit means comprises flexible plastic tube means, and said heat and moisture exchange means includes a wad of flexible material which is capable of absorbing heat and moisture from exhaled air and transferring said heat and moisture to said inhaled air.

10. The patient connection apparatus of claim 9 wherein said wad of flexible material comprises fibrous material.

11. The patient connection apparatus of claim 1 wherein said divider means includes filter means separating said inhalation and exhalation substreams from said patient connection conduit means.

12. The patient connection apparatus according to claim 11, wherein said filter means comprises bacteria filter means for filtering said inhalation and exhalation substreams.

13. The patient connection apparatus of claim 1 wherein said divider means includes intermediate wall means for separating said inhalation substream from said exhalation substream.

14. The patient connection apparatus according to claim 13, wherein said intermediate wall means separates said inhalation and exhalation substreams in said bacteria filter means by forming one portion of said filter exposed to said exhalation substream and another portion of said filter exposed to said inhalation Stream.

15. The patient connection apparatus according to claim 14, wherein said bacteria filter means absorbs at least a part of a medicine exhaled by said patient without substantial increasing resistance to breathing.

16. The patient connection apparatus according to claim 15, wherein a condition of said bacteria filter means is determined by measuring a difference in pressure drop between said portions of said bacteria filter means exposed to said inhalation and exhalation substreams.

17. The patient connection apparatus according to claim 15, wherein said bacteria filter means prevents said exhaled medicine from reaching said respiration-anesthesia device.

18. The patient connection apparatus of claim 1 including inhalation connection means arranged at a position downstream of said heat and moisture exchange means relative to an exhalation direction for connecting said patient connection conduit means to said nebulizer, and non-return valve means disposed in said inhalation connection means for preventing exhaled air from flowing through said inhalation connection means.

19. The patient connection apparatus of claim 1 including inhalation connection means arranged at a position downstream of said heat and moisture exchange means relative to an exhalation direction for connecting said patient connection conduit means to said nebulizer wherein said nebulizer comprises an expansion chamber connected to said inhalation connection means, and reservoir means connected to said expansion chamber for supplying a fluid and/or medication for nebulization therein.

20. The patient connection apparatus of claim 19 wherein said reservoir means includes pressure means for supplying said fluid and/or medication to said expansion chamber.

21. The patient connector apparatus according to claim 1, wherein said nebulizer connection means is located between said patient connection nipple means and said heat and moisture exchange means.

22. A patient connection apparatus for connecting a patient to a respiration or anesthesia device, comprising:

a patient connection nipple for providing an inhalation-exhalation stream, a divider for dividing said inhalation-exhalation stream into an inhalation substream and an exhalation substream, a patient connection conduit for connecting said patient connection nipple to said divider, said patient connection conduit including a flexible plastic tube, a heat and moisture exchanger disposed in said patient connection conduit for exchanging heat and moisture within said inhalation-exhalation stream in such a manner that said heat and moisture exchanger removes heat and moisture from said exhalation substream and delivers said heat and moisture to said inhalation substream, said heat and moisture exchanger including a wad of flexible material capable of absorbing said heat and moisture from said exhalation substream and transferring said heat and moisture to said inhalation substream, said divider including a bacteria filter separating said inhalation and exhalation substreams from said patient connection conduit for filtering said inhalation and exhalation substreams, said divider including an intermediate wall for separating said inhalation and exhalation substreams from one another and for separating said inhalation and exhalation substreams in said bacteria filter by forming one portion of said filter exposed to said exhalation substream and another portion of said filter exposed to said inhalation substream, at least a portion of said bacteria filter exposed to said exhalation substream absorbing at least a part of a medicine exhaled by said patient without substantial increasing resistance to breathing, whereby a condition of said bacteria filter is determined by measuring a difference in pressure drop between said portions of said bacteria filter exposed to said inhalation and exhalation substreams.

23. The patient connection apparatus according to claim 22, further comprising a connection arrangement for connecting said inhalation-exhalation stream with a powder inhalation arrangement, said powder inhalation arrangement associated with said patient connection nipple for supplying a powder to said patient.

24. The patient connection apparatus of claim 22, wherein said bacteria filter prevents said exhaled medicine from reaching said respiration or anesthesia device.

25. A patient connection apparatus for connecting a patient to a respiration or anesthesia device, comprising:

a patient connection nipple for providing an inhalation-exhalation stream, a divider for dividing said inhalation-exhalation stream into an inhalation substream and an exhalation substream, a patient connection conduit for connecting said patient connection nipple to said divider, a heat and moisture exchanger disposed in said patient connection conduit for exchanging heat and moisture within said inhalation-exhalation stream in such a manner that said heat and moisture exchanger removes heat and moisture from said exhalation substream and delivers said heat and moisture to said inhalation substream, a nebulizer, a nebulizer connecting arrangement for connecting said inhalation-exhalation stream to said nebulizer, an inhalation connection arrangement connecting said patient connection conduit to said nebulizer at a position downstream of said heat and moisture exchanger relative to an exhalation direction, said inhalation connector arrangement being removably connected to said patient connection conduit, and a patient connection conduit closure for closing said patient connection conduit upon detachment of said inhalation connection arrangement therefrom.

26. A patient connection apparatus for connecting a patient to a respiration or anesthesia device, comprising:

a patient connection nipple for providing an inhalation-exhalation stream, a divider for dividing said inhalation-exhalation stream into an inhalation substream and an exhalation substream, a patient connection conduit for connecting said patient connection nipple to said divider, a heat and moisture exchanger disposed in said patient connection conduit for exchanging heat and moisture within said inhalation-exhalation stream in such a manner that said heat and moisture exchanger removes heat and moisture from said exhalation substream and delivers said heat and moisture to said inhalation substream, a powder inhalation mechanism associated with said patient connection nipple for supplying a powder to said patient, said powder inhalation mechanism including a hand-actuated gas supply mechanism for supplying gas to said powder inhalation mechanism to aid in supplying said powder to said patient and a container sealingly enclosing said powder inhalation mechanism, said gas supply mechanism including a rubber bladder or rubber bellows, and a powder connecting arrangement for connecting said inhalation-exhalation stream to said powder inhalation mechanism.

27. The patient connection apparatus of claim 26, further comprising a nebulizer and an inhalation connection arrangement arranged at a position downstream of said heat and moisture exchanger relative to an exhalation direction for connecting said patient connection conduit to said nebulizer.

28. The patient connection apparatus of claim 27, wherein said powder inhalation arrangement is associated with said inhalation connection arrangement.

29. The patient connection apparatus of claim 28, wherein said inhalation connection arrangement includes a non-return valve for preventing exhaled air from flowing through said inhalation connection arrangement.

30. A patient connection apparatus for connecting a patient to a respiration or anesthesia device, comprising:

a patient connection nipple for providing an inhalation-exhalation stream, a divider for dividing said inhalation-exhalation stream into an inhalation substream and an exhalation substream, said divider including a bacteria filter interposed between said inhalation and exhalation substreams and said patient connection conduit, a patient connection conduit for connecting said patient connection nipple to said divider, a heat and moisture exchanger disposed in said patient connection conduit for exchanging heat and moisture within said inhalation-exhalation stream in such a manner that said heat and moisture exchanger removes heat and moisture from said exhalation substream and delivers said heat and moisture to said inhalation substream, a powder inhalation mechanism associated with said patient connection nipple for supplying a powder to said patient, and a powder connection arrangement for connecting said inhalation-exhalation stream to said powder inhalation mechanism, said divider including an intermediate wall for separating said inhalation substream from said exhalation substream, said intermediate wall separating said substreams in said bacteria filter by forming one portion of said filter exposed to said exhalation substream and another portion of said filter exposed to said inhalation substream, at least a portion of said bacteria filter exposed to said exhalation substream absorbing at least a part of a medicine exhaled by said patient without substantial increasing resistance to breathing, whereby a condition of said bacteria filter is determined by measuring a difference in pressure drop between said portions of said bacteria filter exposed to said inhalation and exhalation substreams.

31. A patient connection apparatus for connecting a patient to a respiration an anesthesia device, comprising:

a patient connection nipple for providing an inhalation-exhalation stream, a divider for dividing said inhalation-exhalation stream into an inhalation substream and an exhalation substream, a patient connection conduit for connecting said patient connection nipple to said divider, a heat and moisture exchanger disposed in said patient connection conduit for exchanging heat and moisture within said inhalation-exhalation stream in such a manner that said heat and moisture exchanger removes heat and moisture from said exhalation substream and delivers said heat and moisture to said inhalation substream, a powder inhalation mechanism associated with said patient connection nipple for supplying a powder to said patient, said powder inhalation mechanism including a gas supply mechanism for supplying gas to said powder inhalation mechanism to aid in supplying said powder to said patient, and a powder connecting arrangement for connecting said in